US012611277B2

(12) United States Patent (10) Patent No.: US 12,611,277 B2
Ihara et al. (45) Date of Patent: Apr. 28, 2026

(54) STERILE DRAPE, SURGICAL ROBOT, AND METHOD OF ATTACHING STERILE DRAPE

(71) Applicant: MEDICAROID CORPORATION, Kobe (JP)

(72) Inventors: Hiroaki Ihara, Kobe (JP); Mamoru Kono, Kobe (JP); Yuki Sagoi, Kobe (JP); Yuko Mori, Kobe (JP)

(73) Assignee: MEDICAROID CORPORATION, Kobe (JP)

( * ) Notice: Subject to any disclaimer, the term of this patent is extended or adjusted under 35 U.S.C. 154(b) by 492 days.

(21) Appl. No.: 17/840,396

(22) Filed: Jun. 14, 2022

(65) Prior Publication Data

US 2022/0395346 A1     Dec. 15, 2022

(30) Foreign Application Priority Data

Jun. 15, 2021     (JP) .................................. 2021-099646

(51) Int. Cl.
*A61B 46/10*          (2016.01)
*A61B 34/30*          (2016.01)
(52) U.S. Cl.
CPC .............. *A61B 46/10* (2016.02); *A61B 34/30* (2016.02)
(58) Field of Classification Search
None
See application file for complete search history.

(56) References Cited

U.S. PATENT DOCUMENTS

| | | | |
|---|---|---|---|
| 2006/0161137 A1 | 7/2006 | Orban, III et al. | |
| 2015/0202009 A1* | 7/2015 | Nussbaumer | A61B 46/10 128/856 |
| 2017/0086934 A1 | 3/2017 | Devengenzo et al. | |
| 2018/0206931 A1* | 7/2018 | Scheib | A61B 34/70 |
| 2020/0069383 A1* | 3/2020 | Betsugi | A61B 34/25 |
| 2020/0188050 A1* | 6/2020 | Pennoyer | A61B 50/13 |
| 2020/0345440 A1 | 11/2020 | Elmaanaoui et al. | |
| 2021/0153965 A1* | 5/2021 | Lau | A61B 34/30 |

(Continued)

FOREIGN PATENT DOCUMENTS

| | | |
|---|---|---|
| JP | H06-68708 U | 9/1994 |
| JP | 2009-509653 A | 3/2009 |
| JP | 2017-512547 A | 5/2017 |

OTHER PUBLICATIONS

"John Keating, Parts Marking: When All You Need Is a Dot, Assembly, Jul. 31, 2009, https://www.assemblymag.com/articles/86963-parts-marking-when-all-you-need-is-a-dot" (Year: 2009).*

(Continued)

*Primary Examiner* — Michael T. Holtzclaw
(74) *Attorney, Agent, or Firm* — METROLEX IP LAW GROUP, PLLC; Robert L. Scott, Esq.

(57) ABSTRACT

A sterile drape for covering a robot arm of a surgical robot according to an embodiment may include: a bag-shaped drape body formed with an opening at an end portion on one side of the drape body; and a mount cover provided at the other side of the drape body and configured to cover a mount section of the robot arm to which a surgical instrument is to be mounted via an adaptor. The mount cover includes one or more through holes. A protective film that is configured to be peelable from the mount cover is attached to the mount cover so as to cover the one or more through holes.

20 Claims, 8 Drawing Sheets

(56) References Cited

U.S. PATENT DOCUMENTS

| | | | |
|---|---|---|---|
| 2022/0022990 A1* | 1/2022 | Zhang .................... | A61B 34/30 |
| 2022/0087764 A1* | 3/2022 | Levinson .............. | A61B 90/50 |

OTHER PUBLICATIONS

"Hedenqvist, et al., Rubber Elasticity, Dec. 21, 2019, Fundamental Polymer Science Second Edition, Springer, Chapter 3—pp. 75-111" (Year: 2019).*

* cited by examiner

STERILE DRAPE, SURGICAL ROBOT, AND METHOD OF ATTACHING STERILE DRAPE

CROSS REFERENCE TO RELATED APPLICATIONS

This application claims priority to Japanese Patent Application No. 2021-099646 filed on Jun. 15, 2021, the entire contents of which are incorporated herein by reference.

BACKGROUND ART

The disclosure may relate to a sterile drape, a surgical robot, and a method of attaching a sterile drape.

In a related art, there has been known a sterile drape for covering a robot arm of a surgical robot.

Japanese Patent Application Publication No. 2009-509653 discloses a sterile drape including a bag-shaped drape body having an opening at one end portion thereof and a cuff provided integrally with the drape body at the opening of the drape body. An assistant puts his/her hand in the cuff integrally provided with the drape body and pulls the drape body along the robot arm to attach the drape body to the robot arm.

Japanese Patent Application Publication No. 2017-512547 discloses a surgical drape (sterile drape) including a bag-shaped drape body having an opening at one end portion thereof. In the surgical drape disclosed in Japanese Patent Application Publication No. 2017-512547, a magnet is provided on one of a robot arm and the drape body, and an iron-based metal member is provided on the other, so that the magnet and the iron-based metal member are attracted by the magnetic force to fix the drape body to the robot arm.

SUMMARY

The sterile drape disclosed in Japanese Patent Application Publication No. 2009-509653 is provided with a sterile adaptor for attaching a surgical instrument to the robot arm. By the way, in order to provide a sterile drape at a low cost, a sterile drape and a sterilized adaptor may be provided separately. In such a case, the sterile drape is provided with a mount cover with an opening (through hole) at a position corresponding to a mount section of the robot arm. Accordingly, when the sterile drape is attached to the robot arm, a part of the mount section of the robot arm, which is not sterilized, may be exposed through the opening (through hole) of the mount cover. Therefore, the part of the mount section of the robot arm that is exposed through the opening (through hole) of the mount cover might contaminate a clean area and clean objects.

An object of one or more embodiments of the disclosure may be to prevent a clean area and clean objects from being contaminated by part of a robot arm that may be exposed through a through hole of a mount cover of a sterile drape upon attaching the sterile drape to the robot arm.

A first aspect of the disclosure may be a sterile drape for covering a robot arm of a surgical robot. The sterile drape may include: a bag-shaped drape body formed with an opening at an end portion on one side of the drape body; and a mount cover provided at the other side of the drape body and configured to cover a mount section of the robot arm to which a surgical instrument is to be mounted via an adaptor. The mount cover includes one or more through holes, and a protective film that is configured to be peelable from the mount cover is attached to the mount cover so as to cover the one or more through holes.

According to the first aspect, since the protective film is attached to the mount cover so as to cover the one or more through holes of the mount cover, the mount section of the robot arm that is not sterilized is not exposed through the one or more through holes of the mount cover. As a result, it is possible to avoid contamination of the clean area and clean objects upon attaching the sterile drape to the robot arm.

A second aspect of the disclosure may be a surgical robot that may include: a robot arm to which a surgical instrument is to be attached; and a sterile drape configured to cover the robot arm. The sterile drape includes: a bag-shaped drape body formed with an opening at an end portion on one side of the drape body; and a mount cover provided at the other side of the drape body and configured to cover a mount section of the robot arm to which the surgical instrument is to be mounted via an adaptor. The mount cover is formed with one or more through holes. A protective film that is configured to be peelable from the mount cover is attached to the mount cover so as to cover the one or more through holes.

According to the surgical robot of the second aspect, since the protective film is attached to the mount cover so as to cover the one or more through holes of the mount cover, the mount section of the robot arm that is not sterilized is not exposed through the one or more through holes of the mount cover. As a result, it is possible to avoid contamination of the clean area and clean objects upon attaching even the sterile drape to the robot arm.

A third aspect of the disclosure may be a method of attaching a sterile drape for covering a robot arm of a surgical robot. The method may include: covering the robot arm with a bag-shaped drape body of the sterile drape, wherein the drape body is formed with an opening at an end portion on one side of the drape body; fixing the drape body to the robot arm with an annular elastic string provided in the vicinity of the opening of the drape body; peeling a protective film from a mount cover that is provided at the other side of the drape body and covers a mount section of the robot arm; and attaching an adaptor that is configured to mount a surgical instrument to the robot arm to the mount section of the robot arm via the mount cover.

According to the sterile drape attaching method of the third aspect, since the protective film is attached to the mount cover upon attaching the sterile drape to the robot arm, the mount section of the robot arm that is not sterilized is not exposed through the mount cover. As a result, it is possible to reliably preventing the clean area and objects from being contaminated upon attaching the sterile drape to the robot arm.

DETAILED DESCRIPTION

Figure 1:
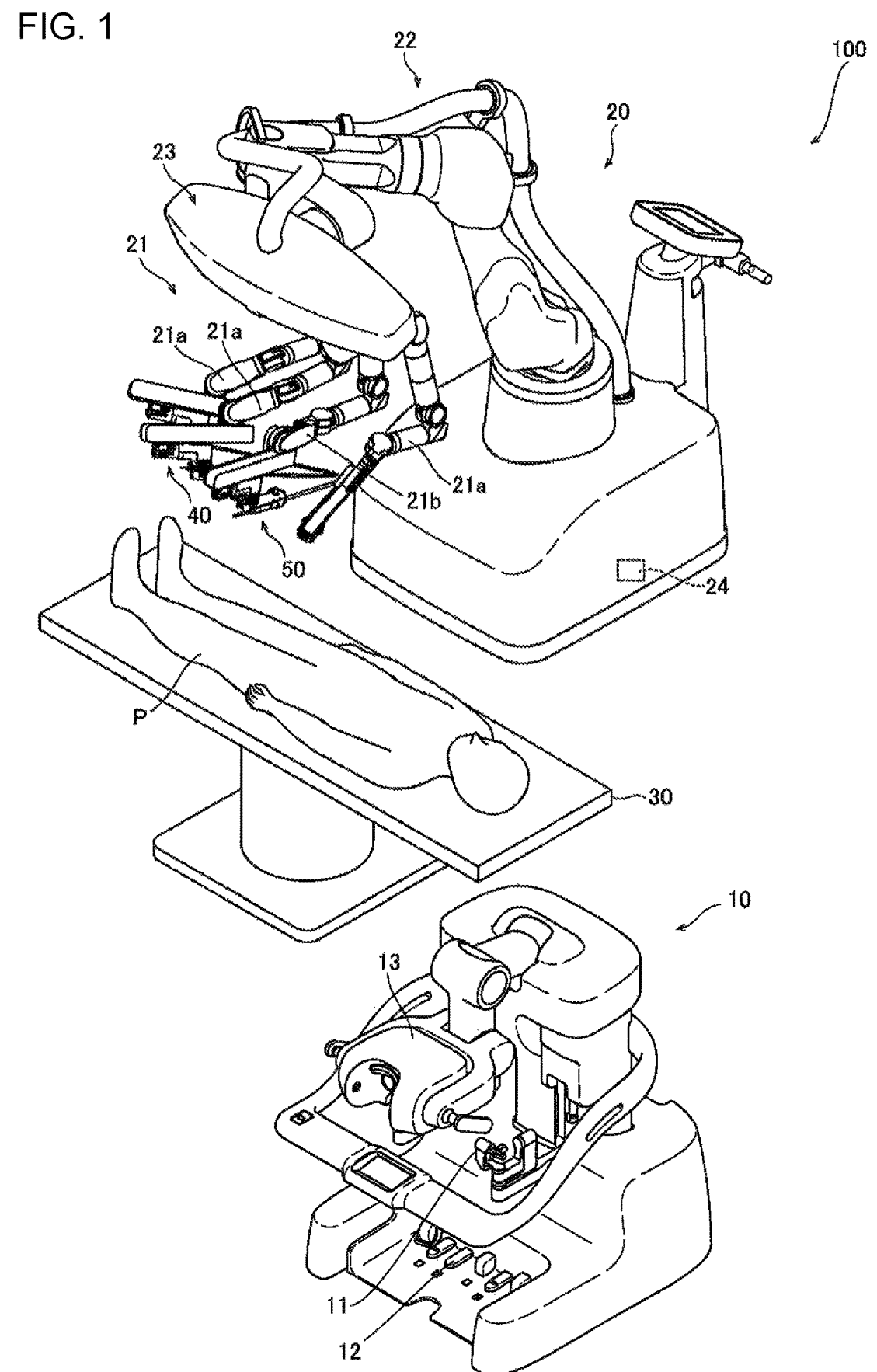
FIG. 1 is a diagram illustrating an overview of a robotic surgical system according to an embodiment.

Descriptions are provided hereinbelow for one or more embodiments based on the drawings. In the respective drawings referenced herein, the same constituents are designated by the same reference numerals and duplicate explanation concerning the same constituents is omitted. All of the drawings are provided to illustrate the respective examples only.

(Configuration of Robotic Surgical System)

A configuration of a robotic surgical system 100 according to an embodiment is described with reference to FIGS. 1 and 2.

As illustrated in FIG. 1, the robotic surgical system 100 includes a remote control apparatus 10 and a patient-side apparatus 20.

The remote control apparatus 10 is provided to remotely control medical equipment provided to the patient-side apparatus 20. When an operator, as a surgeon, inputs an action mode instruction to be executed by the patient-side apparatus 20, to the remote control apparatus 10, the remote control apparatus 10 transmits the action mode instruction to the patient-side apparatus 20 through a controller 24. In response to the action mode instruction transmitted from the remote control apparatus 10, the patient-side apparatus 20 operates the medical equipment, including surgical instruments 40 mounted to robot arms 21*a* and an endoscope 50 mounted to a robot arm 21*b*. This allows minimally invasive surgery. Note that the patient-side apparatus 20 may be an example of a surgical robot.

The patient-side apparatus 20 constitutes an interface to perform a surgery for a patient P. The patient-side apparatus 20 is positioned beside an operation table 30 on which patient P is laid. The patient-side apparatus 20 includes plural robot arms 21*a* and 21*b*. The endoscope 50 is mounted (attached) to one (21*b*) of the robot arms holds, and the surgical instruments 40 are mounted (attached) to the other robot arms (21*a*). The robot arms 21*a* and 21*b* are commonly supported by an arm base 23. Each of the plural robot arms 21*a* and 21*b* includes plural joints. Each joint is provided with a driver provided with a servo-motor and a position detector such as an encoder. The robot arms 21*a* and

21*b* are configured so that the medical equipment mounted to each of the robot arms 21*a* and 21*b* is controlled by a driving signal given through the controller 24 and performs a desired movement.

The arm base 23 is supported by the positioner 22. The positioner 22 includes a vertical articulated robot. The positioner 22 is configured to move the position of the arm base 23 three-dimensionally.

Figure 3:
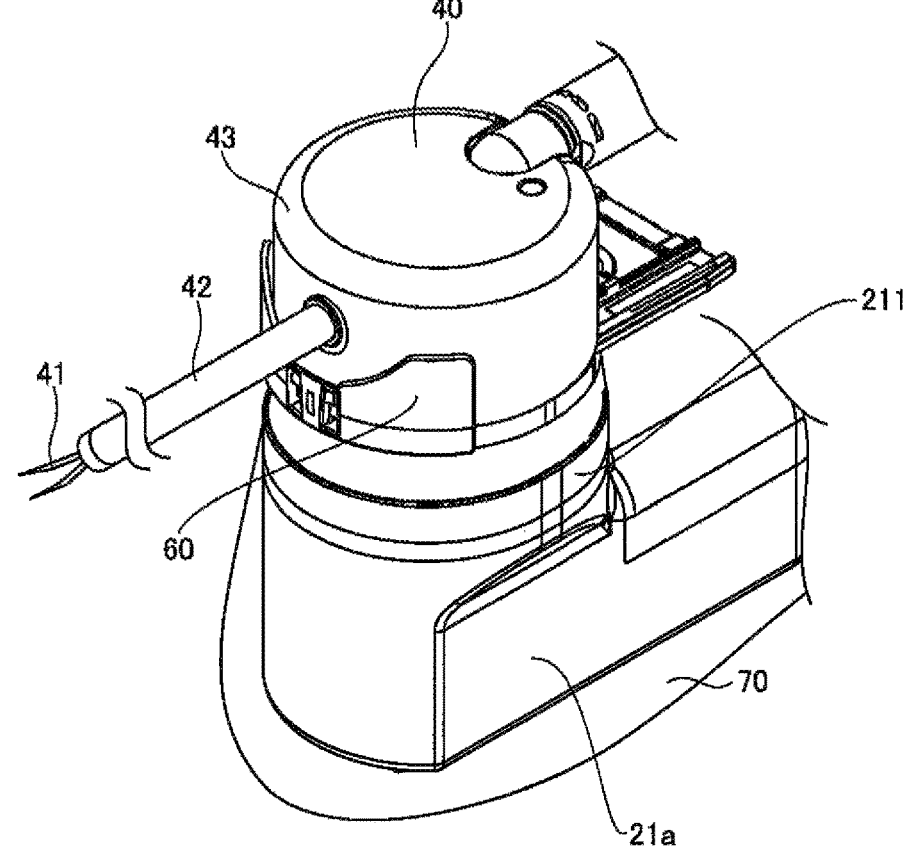
FIG. 3 is a diagram illustrating a perspective view of a state where a surgical instrument is mounted to a robot arm through an adaptor according to an embodiment.

The surgical instruments 40 as the medical equipment are detachably mounted to the distal ends of the robot arms 21*a*. As illustrated in FIG. 3, each surgical instrument 40 includes: a housing 43, which is mounted to the robot arm 21*a*; an elongated shaft 42; and an end effector 41, which is provided at a distal end portion of the shaft 42. Examples of the end effector 41 include gripping forceps, scissors, hooks, high-frequency knives, snare wires, clamps, and staplers. However, the end effector is not limited to these. Various treatment instruments can be applied. In surgeries using the patient-side apparatus 20, the robot arms 21*a* introduce the surgical instruments 40 into the body of the patient P through a cannula (trocar) placed on the body surface of the patient P. The end effectors 41 of the surgical instruments 40 are then located near a surgery site.

As illustrated in FIG. 1, to the distal end of the robot arm 21*b*, the endoscope 50 as the medical equipment is detachably mounted (attached). The endoscope 50 captures an image in a body cavity of the patient P. The captured image is outputted to the remote control apparatus 10. The endoscope 50 is a 3D endoscope capable of capturing a three-dimensional image or a 2D endoscope. In surgeries using the patient-side apparatus 20, the robot arm 21*b* introduces the endoscope 50 into the body of the patient P through a trocar placed on the body surface of the patient P. The endoscope 50 is then located near the surgery site.

The remote control apparatus 10 constitutes the interface with the operator. The remote control apparatus 10 is an apparatus that allows the operator to operate the medical equipment attached to the robot arms 21*a*. Specifically, the remote control apparatus 10 is configured to transmit action mode instructions which are inputted by the operator and are to be executed by the surgical instruments 40 and endoscope 50, to the patient-side apparatus 20 through the controller 24. The remote control apparatus 10 is installed beside the operation table 30 so that the operator can see the condition of the patient P very well while operating the remote control apparatus 10, for example. The remote control apparatus 10 may be configured to transmit action mode instructions via a wireless communication or a wire communication and be installed in a room different from the operation room where the operation table 30 is installed.

The action modes to be executed by the surgical instruments 40 include modes of actions to be taken by each surgical instrument 40 (a series of positions and postures) and actions to be executed by the function of each surgical instrument 40. When the surgical instrument 40 is a pair of grasping forceps, for example, the action modes to be executed by the surgical instrument 40 include roll and pitch positions of the wrist of the end effector 41 and actions to open and close the jaws. When the surgical instrument 40 is a high-frequency knife, the action modes to be executed by the surgical instrument 40 include vibration of the high-frequency knife, specifically, supply of current to the high-frequency knife. When the surgical instrument 40 is a snare wire, the action modes to be executed by the surgical instrument 40 include a capturing action and an action to release the captured object. Further, the action modes may include an action to supply current to a bipolar or monopolar instrument to burn off the surgery site.

The action modes to be executed by the endoscope 50 include the position and posture of the distal end of the endoscope 50 and setting of the zoom magnification, for example.

Figure 2:
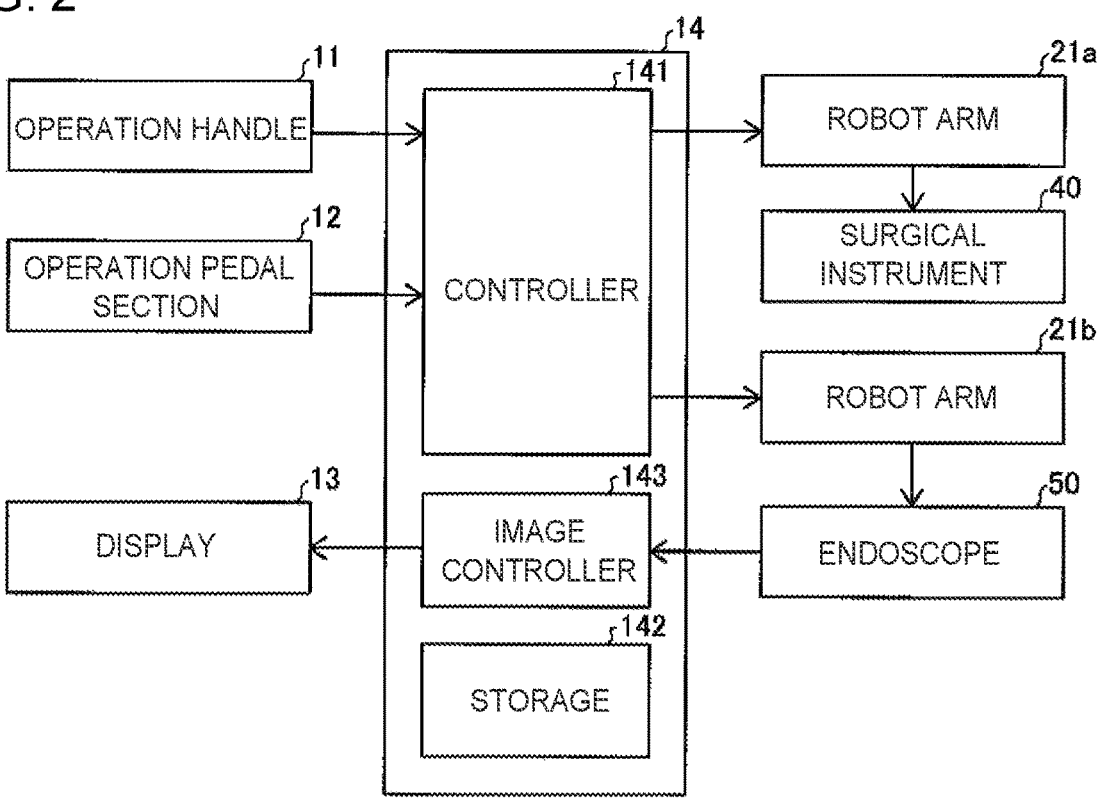
FIG. 2 is a block diagram illustrating a view of a control-related configuration of the robotic surgical system according to an embodiment.

As illustrated in FIGS. 1 and 2, the remote control apparatus 10 includes operation handles 11, an operation pedal section 12, a display 13, and a control apparatus 14.

The operation handles 11 are provided in order to remotely operate medical equipment attached to the robot arms 21a. Specifically, the operation handles 11 accept operations by the operator for operating the medical equipment (the surgical instruments 40 and endoscope 50). The operation handles 11 are composed of two operation handles 11 arranged side by side in the horizontal direction. One of the two operation handles 11 is operated by the right hand of the operator while the other operation handle 11 is operated by the left hand of the operator.

The operation handles 11 extend from the rear side of the remote control apparatus 10 toward the front side. The operation handles 11 are configured to move in a predetermined three-dimensional operation region. Specifically, the operation handles 11 are configured so as to move up and down, right and left, and forward and rearward.

The remote control apparatus 10 and patient-side apparatus 20 constitute a master-slave system in terms of controlling movement of the robot arms 21a and robot arm 21b. The operation handles 11 constitute an operating part on the master side in the master-slave system, and the robot arms 21a and 21b holding the medical equipment constitute an operating part on the slave side. When the operator operates the operation handles 11, the movement of one of the robot arms 21a or 21b is controlled so that the distal end portion (the end effector 41 of the surgical instrument 40) of the robot arm 21a or the distal end portion (the endoscope 50) of the robot arm 21b moves following the movement of the operation handles 11.

The patient-side apparatus 20 controls the movement of the robot arms 21a in accordance with the set motion scaling ratio. When the motion scaling ratio is set to 1/2, for example, the end effectors 41 of the surgical instruments 40 move ½ of the movement distance of the operation handles 11. This allows for precise fine surgery.

The operation pedal section 12 or an operation pedal unit includes plural pedals to execute medical equipment-related functions. The plural pedals include a coagulation pedal, a cutting pedal, a camera pedal, and a clutch pedal. The plural pedals are operated by a foot of the operator.

The coagulation pedal enables the surgical instrument 40 to coagulate a surgery site. Specifically, when the coagulation pedal is operated, voltage for coagulation is applied to the surgical instrument 40 to coagulate the surgery site. The cutting pedal enables the surgical instrument 40 to cut the surgery site. Specifically, the cutting pedal is operated to apply voltage for cutting to the surgical instrument 40 and cut a surgery site.

The camera pedal is used to control the position and orientation of the endoscope 50 that captures images within the body cavity. Specifically, the camera pedal enables operation of the endoscope 50 by the operation handles 11. That is, the position and orientation of the endoscope 50 are controllable by the operation handles 11 while the camera pedal is being pressed. The endoscope 50 is controlled by using both of the right and left operation handles 11, for example. Specifically, when the operator rotates the right and left operation handles 11 about the middle point between the right and left operation handles 11, the endoscope 50 is rotated. When the operator presses the right and left operation handles 11 together, the endoscope 50 goes forward into the body cavity. When the operator pulls the right and left operation handles 11 together, the endoscope 50 goes back. When the operator moves the right and left operation handles 11 together up, down, right, or left, the endoscope 50 moves up, down, right, or left, respectively.

The clutch pedal is used to temporarily disconnect operation-related connection between the operation handles 11 and the robot arms 21a to stop movement of the surgical instruments 40. Specifically, when the clutch pedal is being pressed, the robot arms 21a of the patient-side apparatus 20 do not work even if the operation handles 11 are operated. For example, when the operation handles 11 are operated and moved to the edge of the range of movement, the operator operates the clutch pedal to temporarily disconnect the operation-related connection and then returns the operation handles 11 to the center of the range of movement. When the operator stops operating the clutch pedal, the operation handles 11 are again connected to the robot arms 21a. The operator restarts the operation for the operation handles 11 around the center thereof.

The display 13 (or a display device) is configured to display images captured by the endoscope 50. The display 13 includes a scope type display or a non-scope type display. The scope type display is a display configured in such a manner that the operator looks into the display. The non-scope type display is a display like an open-type display that includes a flat screen such that the operator is able to see without looking into, such as normal displays for personal computers.

When the scope type display is attached, the scope type display displays 3D images captured by the endoscope 50 attached to the robot arm 21b of the patient-side apparatus 20. When the non-scope type display is attached, the non-scope type display also displays 3D images captured by the endoscope 50 provided for the patient-side apparatus 20. The non-scope type display may display 2D images captured by the endoscope 50 provided for the patient-side apparatus 20.

As illustrated in FIG. 2, the control apparatus 14 includes a controller 141, a storage 142, and an image controller 143, for example. The controller 141 includes a calculator such as a CPU. The storage 142 includes a memory, such as a ROM and a RAM. The control apparatus 14 may be composed of a single controller performing centralized control or may be composed of plural controllers that perform decentralized control in cooperation with each other. The controller 141 determines whether an action mode instruction inputted by the operation handles 11 is to be executed by the robot arms 21a or to be executed by the endoscope 50, depending on the state of the operation pedal section 12. When determining that the action mode instruction inputted by the operation handles 11 is to be executed by any one of the surgical instruments 40, the controller 141 transmits the action mode instruction to the corresponding robot arm 21a. The robot arm 21a is thereby driven for controlling movement of the surgical instrument 40 attached to the robot arm 21a.

When determining that the action mode instruction inputted by the operation handles 11 is to be executed by the endoscope 50, the controller 141 transmits the action mode instruction to the robot arm 21b. The robot arm 21b is thereby driven for control of movement of the endoscope 50 attached to the robot arm 21b.

The storage 142 stores control programs corresponding to the types of the surgical instrument 40, for example. The controller 141 reads the stored control programs according to the types of the attached surgical instruments 40. The action mode instructions from the operation handles 11 and/or the operation pedal section 12 of the remote control apparatus 10 thereby cause the respective surgical instruments 40 to perform proper movements.

The image controller 143 transmits images acquired by the endoscope 50 to the display section 13. The image controller 143 performs processing and alternations for the images when needed.

As illustrated in FIG. 3, the surgical instrument 40 is attached to the robot arm 21a. Each of the robot arms 21 is used in a clean area and is thus covered with a drape 70. Also, the arm base 23 is used in the clean area and is thus covered with a drape. In operation rooms, clean technique is used in order to prevent surgical incision sites and the medical equipment from being contaminated by pathogen, foreign matters, or the like. The clean technique defines a clean area and a contaminated area, which is outside the clean area. The surgery sites are located in the clean area. Members of the surgical team, including the operator, make sure that only sterile objects are placed in the clean area during surgery and perform sterilization for an object which is to be moved to the clean area from the contaminated area. Similarly, when the members of the surgical team including the operator place their hands in the contaminated area, the members sterilize their hands before directly touching objects located in the clean area. Instruments used in the clean area are sterilized or are covered with the drapes 70 that are sterilized. Each of the drapes 70 may be an example of a sterile drape.

The drape 70 is arranged between the robot arm 21 and the surgical instrument 40 or the endoscope 50. Specifically, the drape 70 is arranged between the adaptor 60 and the robot arm 21. The adaptor 60 is attached to the robot arm 21 with the drape 70 being sandwiched between the adaptor 60 and the robot arm 21. Specifically, the adaptor 60 is a drape adaptor that puts the drape 70 between the adaptor 60 and the robot arm 21. The surgical instrument 40 is attached to the adaptor 60 that is attached to the robot arm 21a with the drape 70 interposed therebetween. The robot arm 21a transmits driving force to the surgical instrument 40 through the adaptor 60 to drive the end effector 41 of the surgical instrument 40. Note that although not illustrated, the drape 70 is also arranged between the robot arm 21b and an endoscope adaptor to which the endoscope 50 is attached.

(Drape)

Figure 4:
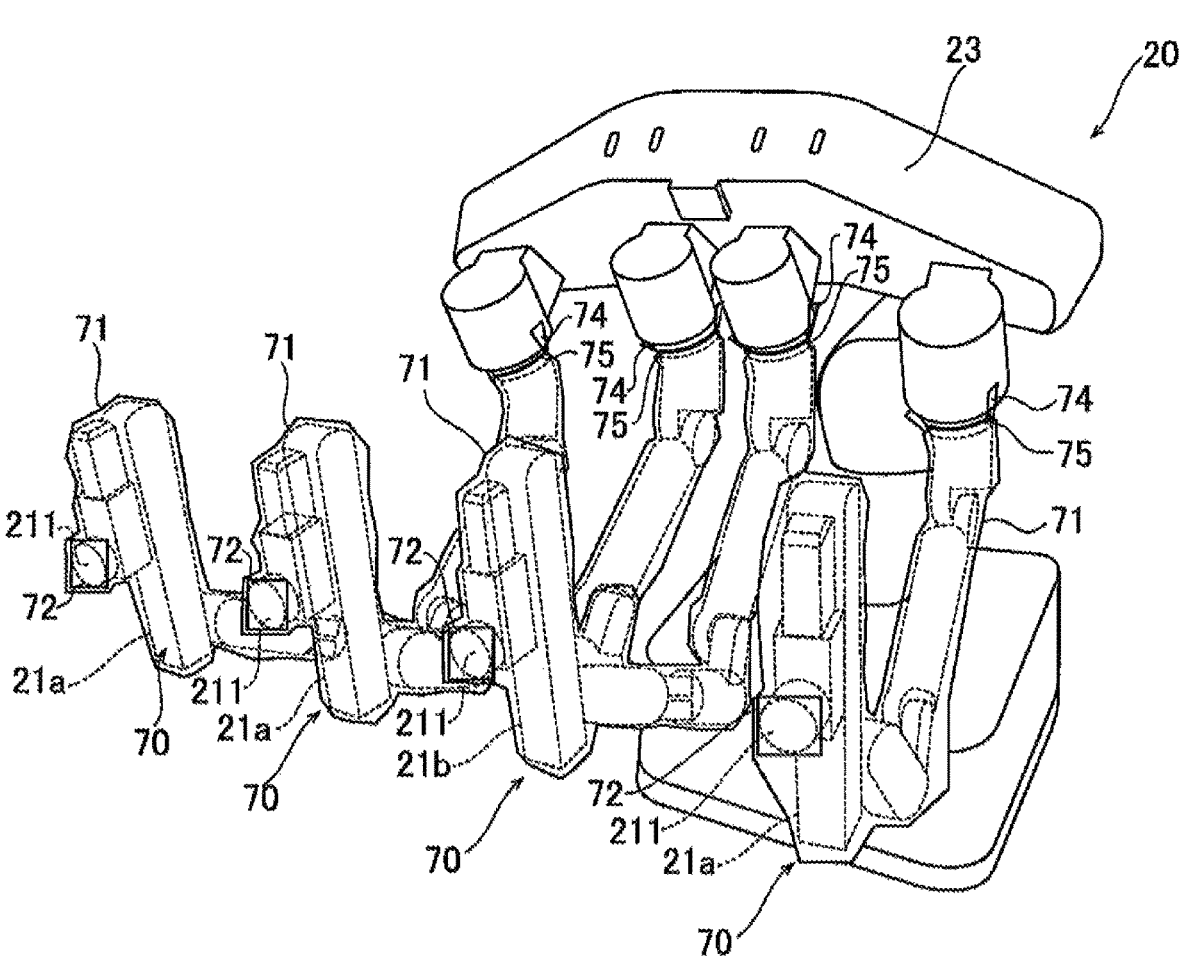
FIG. 4 is a diagram illustrating a perspective view of a state where a drape is attached to the robot arm according to an embodiment.
Figure 5:
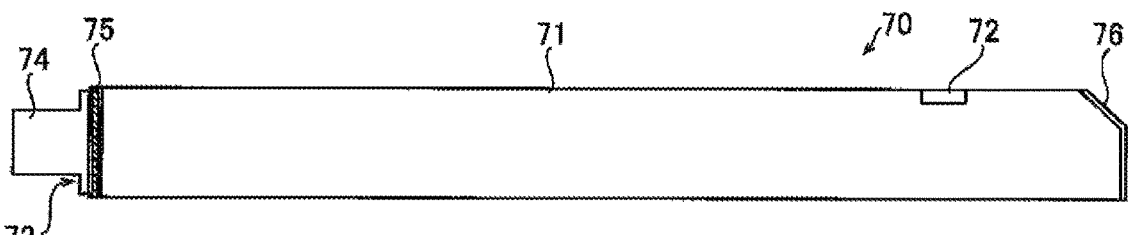
FIG. 5 is a diagram illustrating a side view of the drape, which is to be attached to the robot arm, according to an embodiment.
Figure 6:
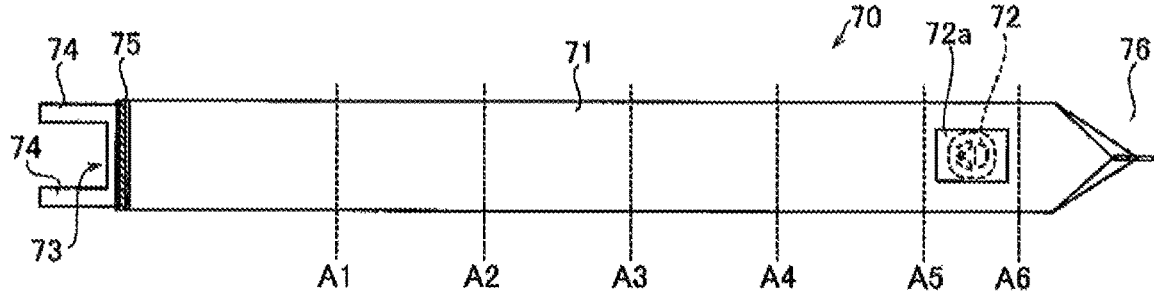
FIG. 6 is a diagram illustrating a plan view of the drape, which is to be attached to the robot arm, according to an embodiment.

As illustrated in FIGS. 3 and 4, the drapes 70 are configured to cover the robot arms 21a and the robot arm 21b. As illustrated in FIGS. 5 and 6, each of the drapes 70 includes a drape body 71 (a drape main body), a mount cover 72, an opening 73, a pair of grip portions 74, and an elastic string 75.

The drape body 71 covers the robot arm 21. The drape body 71 is a flexible film. The drape body 71 is made of a resin material such as low-density polyethylene. Further, the drape body 71 is formed in a thin film shape. The drape body 71 is a colorless and transparent.

The drape body 71 is provided with the opening 73 at an end of the drape body 71 on one side of the drape body 71. Further, the other end of the drape body 71, which is provided on the side opposite to the opening end 73, is closed. In other words, the drape body 71 is formed in an elongate bag shape (a sleeve shape) in which the one end portion of the drape body 71 in a longitudinal direction thereof is opened and the other end portion of the drape body 71 in the longitudinal direction is closed.

Figure 9:
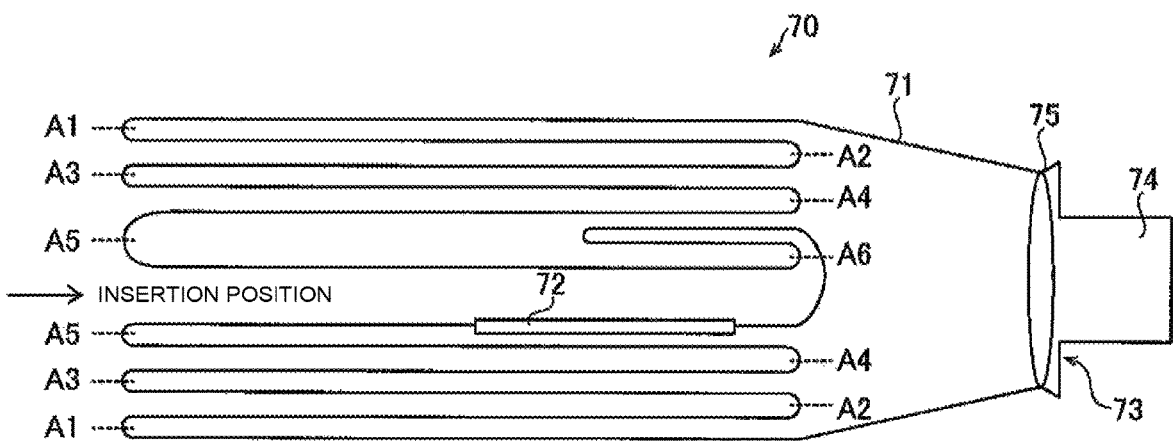
FIG. 9 is a diagram illustrating a state where the drape, which is to be attached to the robot arm, is folded according to an embodiment.

As illustrated in FIG. 9, in a state before the drape body 71 is attached to and covers the robot arm 21, the drape body 71 is folded inward in such a manner that an outer surface of the drape body 71, which is to be exposed to the outside in a state where the drape body 71 covers the robot arm 21, is not exposed to the outside. That is, before use, the outer surface of the drape body 71, which will be exposed to the outside when the drape body 71 covers the robot arm 21, is folded inward so as not to be exposed to the outside. With this configuration, it is possible to prevent the outer surface of the drape body, which is to be arranged in (exposed to) the clean area, from being contaminated before the drape body 71 is attached to the robot arm 21. Further, the drape 70 in the folded state is housed in a sterilized bag before use. For example, the drape 70 is housed in the sterilized bag made of high density polyethylene non-woven fabric (such as Tyvek or the like). Then, when the drape 70 is to be used, the drape 70 is taken out of the sterilized bag and is then attached to the robot arm 21. Note that the drape 70 is sterilized with ethylene oxide gas.

Figure 7:
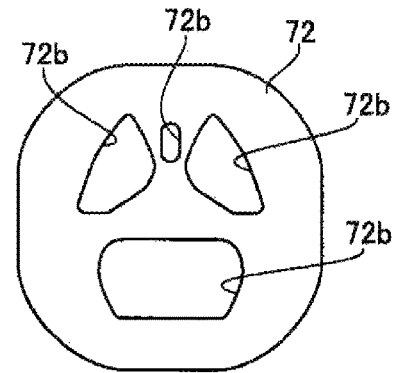
FIG. 7 is a diagram illustrating a plan view of a mount cover of the drape according to an embodiment.

The mount cover 72 is provided at a portion of the drape body 71 on the other side of the drape body 71. Further, the mount cover 72 is configured to cover a mount section 211 of the robot arm 21 to which the adaptor 60 that is configured to mount the surgical instrument 40 to the robot arm 21 is to be mounted. The mount cover 72 has a shape that matches (corresponds to) the shape of the outline of the mount section 211 of the robot arm 21. The mount cover 72 is made of a resin material such as polycarbonate, polyethylene terephthalate or the like. The mount cover 72 is formed in a flat plate shape and is, for example, substantially colorless and transparent. As illustrated in FIG. 7, the mount cover 72 include a plurality of openings (through holes) 72b through which transmission members that are configured to transmit the driving force from the mount section 211 of the robot arm 21 to the surgical instrument 40 via the adaptor 60 and engagement portions that are configured to engage the mount section 211 of the robot arm 21 with the adaptor 60 pass.

As illustrated in FIG. 6, a protective film 72a is attached to the mount cover 72 so as to be peelable (detachable) from the mount cover 72. The protective film 72a is peeled off after the drape body 71 is attached to the robot arm 21 and before the adaptor 60 is attached to the mount section 211 of the robot arm 21 via the mount cover 72. Accordingly, it is possible to prevent the clean area outside the drape body 71 from leading to the contaminated area inside the drape body 71. The protective film 72a is formed of a resin material such as low-density polyethylene or the like. The protective film 72a has a different color from the drape body 71 so as to be distinguishable from the drape body 71. For example, the protective film 72a is colored and transparent. Specifically, the protective film 72a is a light blue transparent. As a result, the position of the mount cover 72 to which the protective film 72a is attached can be easily recognized with respect to the drape body 71. Therefore, when the drape body 71 is to be attached to the robot arm 21, the mount cover 72 can be easily located at the position of the mount section 211 of the robot arm 21.

Here, in an embodiment, the pair of grip portions 74 are provided extending from the one end portion of the drape body 71, as illustrated in FIGS. 5 and 6. That is, the pair of grip portions 74 are arranged at the end of the drape body 71 on the side where the opening 73 is provided. As a result, a worker such as an assistant in surgery pulls the one end of the drape body 71 along the robot arm 21 while grabbing the pair of grip portions 74, so that the robot arm 21 can be easily covered with the drape 70.

As illustrated in FIG. 6, the pair of grip portions 74 are arranged so as to face each other in the direction of sandwiching the mount cover 72 along the direction orthogonal to the longitudinal direction of the drape body 71. Accordingly, in a state where the mount cover 72 is arranged at the position of the mount section 211 of the robot arm 21, the pair of grip portions 74 are gripped with both hands of the worker in such a manner that the mount cover 72 is located between the pair of grip portions 74 and are then pulled along the robot arm 21, so that the one end portion of the drape body 71 can be moved along the robot arm 21. As a result, the one end (the opening end 73) of the drape body 71 can be moved in a well-balanced manner. Therefore, the drape body 71 can be easily attached to the robot arm 21 while suppressing the drape body 71 from being twisted or the like.

The pair of grip portions 74 are formed of a material same as that of the drape body 71 and formed integrally with the drape body 71. As a result, it is possible to easily form the pair of grip portions 74 to the drape body 71 and to suppress an increase in the number of parts as compared with a case where the pair of grip portions 74 are provided separately from the drape body 71.

Here, in an embodiment, the elastic string 75 is provided in the vicinity of the opening end 73 of the drape body 71. The elastic string 75 is configured to fix the drape body 71 to the robot arm 21. Specifically, the elastic string 75 is formed in an annular shape or a ring shape. The elastic string 75 is configured to be elastically deformable. For example, the elastic string 75 comprises a rubber string. That is, the diameter of the annular elastic string 75 can be increased by pulling the annular elastic string 75, and the diameter of the annular elastic string 75 becomes smaller (natural length) when not being pulled. The diameter of the annular elastic string 75 at the natural length is smaller than the diameter of the robot arm 21. With this configuration, the drape body 71 can be easily fixed to the robot arm 21 by the tightening force due to the contraction of the annular elastic string 75.

Further, the annular elastic string 75 is provided at a connection portion of the pair of grip portions 74 to the drape body 71. That is, the annular elastic string 75 is provided in the vicinity of the pair of grip portions 74. With this configuration, the annular elastic string 75 can be expanded by using the pair of grip portions 74. Therefore, when the drape body 71 is to be attached to the robot arm 21, it is possible to prevent the annular elastic string 75 from being caught (stuck) by the robot arm 21.

The annular elastic string 75 has a color different from the drape body 71 so as to be distinguishable from the drape body 71. For example, the annular elastic string 75 is colored and opaque. The annular elastic string 75 has a blue color. With this configuration, the position of the elastic string 75 provided in the vicinity of the opening 73 of the drape body 71 can be easily recognized. Thus, when the drape body 71 is to be attached to the robot arm 21, the position of the opening 73 can be easily recognized.

Figure 8:
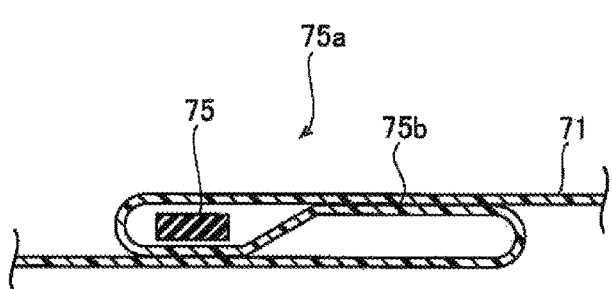
FIG. 8 is a diagram illustrating an enlarged sectional view of an elastic string of the drape according to an embodiment.

As illustrated in FIG. 8, the annular elastic string 75 is arranged in an accommodation portion 75a. The accommodation portion 75a is formed by folding a part of the drape body 71 and heat-welding a welding portion 75b. That is, the accommodation portion 75a is formed of the same material as the drape body 71 and integrally formed with the drape body 71.

The other end of the drape body 71 is linearly closed. The drape body 71 has a shape in which a corner of the other end of the drape body 71 is chamfered. Specifically, as illustrated in FIG. 5, a chamfered portion 76 is provided at the other end (the closed end) of the drape body 71 so as to be tapered toward the side where the mount cover 72 is provided. As a result, the end portion of the drape body 71 on the side to which the surgical instrument 40 is attached is tight (narrowed), so that it is possible to prevent the drape body 71 from dubbing and interfering with the surgical instrument 40 and the worker.

Figure 11:
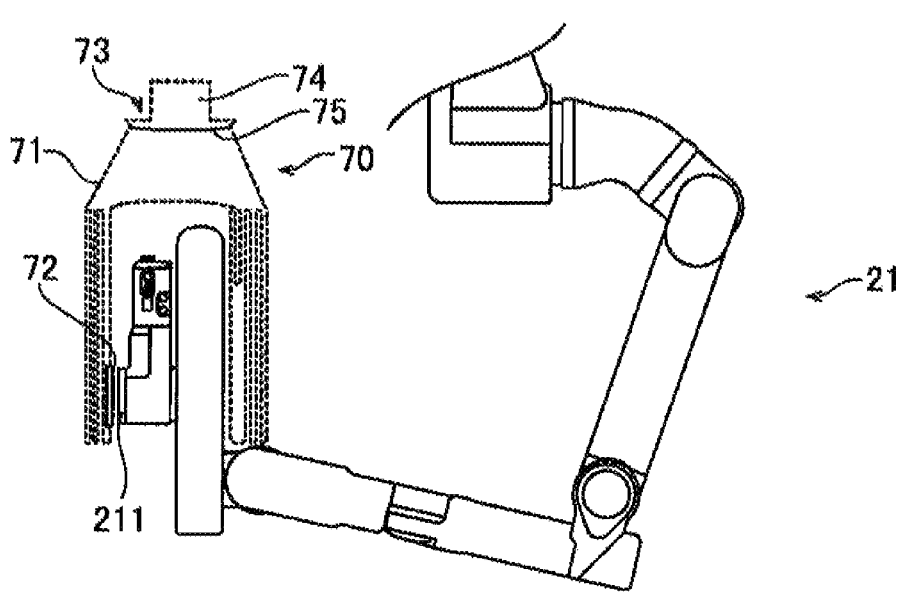
FIG. 11 is a diagram illustrating a state where the robot arm is inserted in the drape from an insertion position of the drape according to an embodiment.

As illustrated in FIGS. 6 and 9, in the state before use, the drape body 71 is folded at a plurality of folding lines A1, A2, A3, A4, A5 and A6. The drape body 71 is folded inward by valley folds at the folding lines A1, A3 and A5. The drape body 71 is folded inward by mountain folds at the folded lines A2 and A4. Further, in the folded line A6, the other end portion of the drape body 71 is folded back to the folded line A5 side. The folded drape body 71 is configured to have a shape having an insertion opening (an insertion position) defined by the annular folding line A5 of the folded drape body 71 where the robot arm 21 is to be inserted therefrom. That is, as illustrated in FIG. 11, the folded drape body 71 is put on the robot arm 21 in a state where the insertion opening (the insertion position) defined by the folding line A5 is widened.

(Method of Attaching Drape)

With reference to FIGS. 10 to 14, a method of attaching the sterile drape 70 to the robot arm 21 of the patient-side apparatus 20 so as to cover the robot arm 21 with the drape 70 is described below. The drape 70 is put on (attached to) the robot arm 21 by the worker (such as a nurse who is an assistant to the surgeon or the like).

In this sterile drape attaching method, the pair of grip portions 74 extending from the one end (the opening end 73) of the bag-shaped drape body 71 are gripped and pulled along the robot arm 21 so as to cover the robot arm 21 with the drape body 71, and then the drape body 71 is fixed to the robot arm 21 by means of the annular elastic string 75 provided in the vicinity of the opening end 73 of the drape body 71.

With this sterile drape attaching method, from the state where the drape body 71 is folded inward in such a manner that the outer surface of the drape body 71 is not exposed, the opening end 73 of the drape body 71 is pulled along the robot arm 21 while the folded drape body 71 is being turned inside out (unfolded), so that the robot arm 21 is covered with drape body 71.

Figure 10:
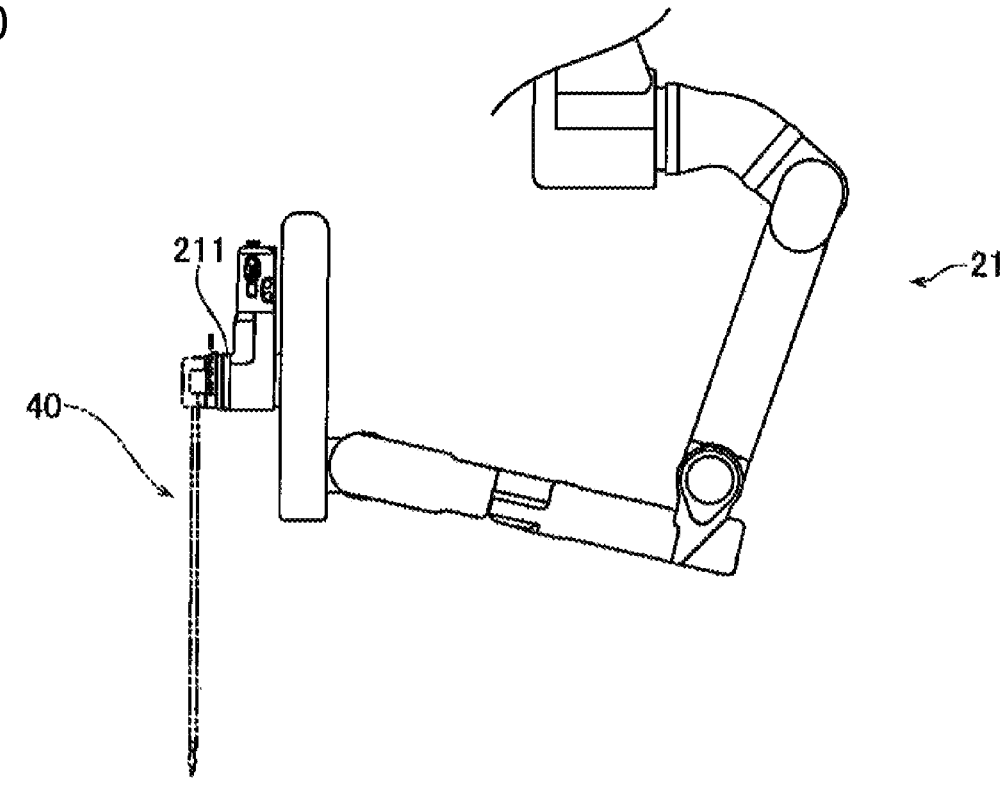
FIG. 10 is a diagram illustrating a view of the robot arm when the drape is to be attached to the robot arm according to an embodiment.

Specifically, as illustrated in FIG. 10, the distal end of the robot arm 21 is set upright. That is, when the surgical instrument 40 is attached to the mount section 211 of the robot arm 21, the robot arm 21 is in a posture in which the surgical instrument 40 extends downward.

Next, as illustrated in FIG. 11, the drape 70 with the drape body 71 being folded is put on the distal end of the robot arm 21. At this time, as illustrated in FIG. 9, the insertion opening (the insertion gap) of the drape body 71 is widened and the robot arm 21 is then inserted into the drape body 71 through the insertion opening of the drape body 71. Further at this time, the drape body 71 is put on the robot arm 21 in such a manner that the mount cover 72 of the drape 70 faces the mount section 211 of the robot arm 21.

Figure 12:
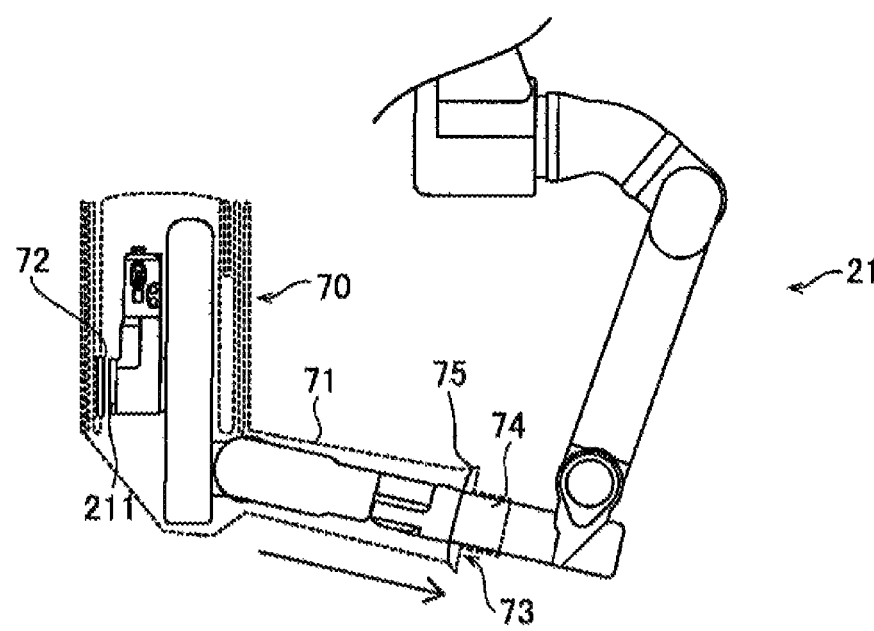
FIG. 12 is a diagram illustrating a first state where grip portions of the drape are pulled along the robot arm according to an embodiment.
Figure 13:
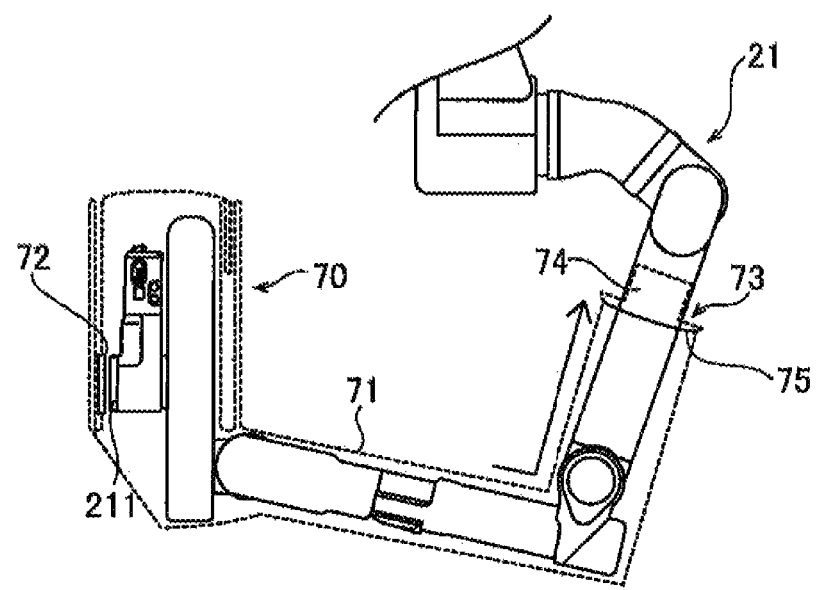
FIG. 13 is a diagram illustrating a second state where the grip portions of the drape are pulled along the robot arm according to an embodiment.

Next, as illustrated in FIGS. 12 and 13, while the pair of grip portions 74 of the drape 70 are gripped, the pair of grip portions 74 (the opening end 73) are moved (pulled) along the robot arm 21. As a result, the drape body 71 folded inward is turned inside out. Further, by moving (pulling) the pair of grip portions 74 along the robot arm 21, the folded drape body 71 is unfolded gradually so as to cover the robot arm 21 with the unfolded drape body 71. In this case, the pair of grip portions 74 may be moved along the robot arm 21, in a state where a distance between the pair of grip portions 74 being gripped are widen and thus the diameter of the elastic string 75 is expanded.

Figure 14:
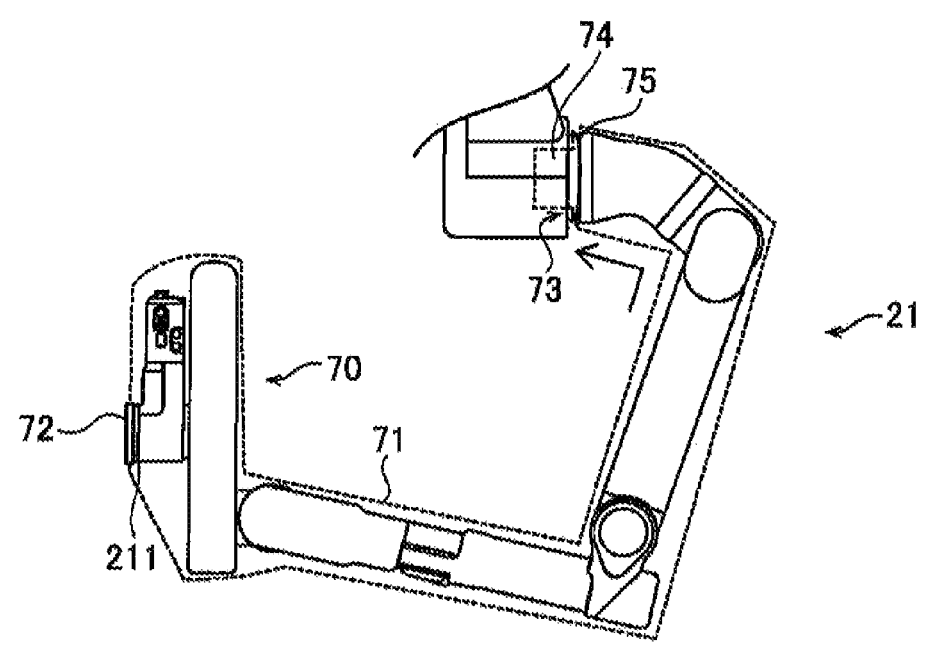
FIG. 14 is a diagram illustrating a view of a state where the drape is attached to and covers the robot arm according to an embodiment.

Next, as illustrated in FIG. 14, when the pair of grip portions 74 (the opening end 73) of the drape 70 reach the proximal end portion of the robot arm 21, the pair of grip portions 74 are released. Thus, the annular elastic string 75 is elastically deformed to return to the original shape, so that the one end portion (the opening end 73) of the drape body 71 is fixed to the proximal end portion of the robot arm 21 by the annular elastic string 75. The proximal end portion of the robot arm 21 is provided with an annular groove, and thus the one end (the opening end 73) of the drape body 71 is fixed to the proximal end portion of the robot arm 21 by means of the annular elastic string 75 fitting in the annular groove. As a result, the robot arm 21 is covered with the drape body 71. The outer surface of the drape body 71 in this state is a sterilized surface, so that the robot arm 21 being covered with the drape 70 can be arranged in the clean area.

The drapes 70 are sequentially put on the plural robot arms 21. Then, the protective film 72a covering the mount cover 72 is peeled off from the drape 70 put on the robot arm 21 so as to expose the through holes of the mount cover 72, and then the adaptor 60 is attached to the mount section 211 of the robot arm 21 via the through holes of the mount cover 72. After that, the surgical instrument 40 is mounted to the adaptor 60.

(Modifications)

Note that one or more embodiments disclosed herein should be considered as exemplary in all respects and do not limit the invention. The scope of the invention is indicated by claims, not by explanation of one or more embodiments described above, and includes equivalents to the claims and all alterations (modification) within the same.

For example, in one or more embodiments described above, the case has been described in which the drape body is colorless and transparent. However, the invention is not limited to this. In the invention, a drape body may be colored transparent, or may be translucent. Further, a drape body may be opaque.

In one or more embodiments described above, the case has been described in which the four robot arms are provided to the patient-side apparatus (surgical robot). However, the invention is not limited thereto. In the invention, a surgical robot may be provided with three or less or five or more robot arms.

In one or more embodiments described above, the case has been described in which the pair of grip portions are integrally formed with the drape body. However, the invention is not limited thereto. In the invention, a pair of grip portions may be formed as a member(s) different from a drape body and ] be attached to one end of the drape body.

In one or more embodiments described above, the case has been described in which the elastic string is arranged in the accommodation portion which is formed by folding the drape body. However, the invention is not limited thereto. In the invention, an accommodation portion may be formed by a member(s) different from a drape body. Further, an elastic string may be adhered to a drape body without providing an accommodation portion to the drape.

In one or more embodiments described above, the case has been described in which the elastic string comprises the rubber string. However, the invention is not limited thereto. In the invention, an elastic string may be formed of a material such as an elastic resin or the like other than rubber. Further, an elastic string may comprise a coil spring formed in a string shape.

In one or more embodiments described above, the case has been described in which the adaptor and the drape are provided independently of each other. However, the invention is not limited thereto. For example, an adaptor and a drape may be provided integrally with each other.

The invention claimed is:

1. A sterile drape for covering a robot arm of a surgical robot, comprising:

a bag-shaped drape body formed with an opening at an end portion on one side of the drape body;

a pair of grip portions projecting outside from the end portion on the one side of the drape body in a direction parallel to a longitudinal direction of the drape body and formed integrally with the drape body; and a mount cover that is provided at the other side of the drape body and is a flat resin plate including a first surface and a second surface opposite to the first surface, the first surface facing a mount section of the robot arm and the second surface facing an adaptor that attaches the mount cover to the mount section and to which a surgical instrument is to be mounted, wherein the mount cover includes a plurality of through holes and is provided independently of the adaptor, a protective film is attached to the second surface of the mount cover so as to cover all of the plurality of through holes, the protective film being configured to be peelable from the mount cover, and a length of the protective film is longer than a length of the mount cover in the longitudinal direction.

2. The sterile drape according to claim 1, wherein the drape body and the protective film are in different colors so as to be distinguishable from each other.

3. The sterile drape according to claim 2, wherein the drape body is colorless and transparent, and the protective film is colored.

4. The sterile drape according to claim 3, wherein the mount cover is colorless and transparent.

5. The sterile drape according to claim 1, further comprising an annular elastic string provided in the vicinity of the opening of the drape body and configured to fix the drape body to the robot arm.

6. The sterile drape according to claim 5, wherein the annular elastic string is provided at a connection portion of the pair of grip portions to the drape body.

7. The sterile drape according to claim 5, wherein the drape body and the annular elastic string are in different colors so as to be distinguishable from each other.

8. The sterile drape according to claim 7, wherein the drape body is colorless and transparent, and the annular elastic string is colored.

9. The sterile drape according to claim 5, wherein the annular elastic string comprises a rubber string.

10. The sterile drape according to claim 1, wherein the pair of grip portions are arranged facing each other in a direction sandwiching the mount cover along a direction orthogonal to the longitudinal direction of the drape body.

11. The sterile drape according to claim 1, wherein the pair of grip portions are formed of a same material as the drape body and formed integrally with the drape body.

12. The sterile drape according to claim 1, wherein
in a state before the drape body covers the robot arm, the
drape body is folded inward in such a manner that an
outer surface of the drape body, which is to be exposed
to the outside in a state where the drape body covers the
robot arm, is not exposed to the outside.

13. The sterile drape according to claim 1, wherein
the drape body has a shape in which an end portion on the
other side of the drape body is linearly closed, wherein
a corner of the end portion on the other side of the drape
body is chamfered.

14. The sterile drape according to claim 1, wherein
the protective film is peeled off after covering the robot
arm with the drape body and before attaching the
adaptor to the mount section of the robot arm via the
mount cover.

15. A surgical robot comprising:
a robot arm to which a surgical instrument is to be
attached; and
a sterile drape configured to cover the robot arm, wherein
the sterile drape comprises:
a bag-shaped drape body formed with an opening at an
end portion on one side of the drape body;
a pair of grip portions projecting outside from the end
portion on the one side of the drape body in a direction
parallel to a longitudinal direction of the drape body
and formed integrally with the drape body; and
a mount cover that is provided at the other side of the
drape body and is a flat resin plate including a first
surface and a second surface opposite to the first
surface, the first surface facing a mount section of the
robot arm and the second surface facing an adaptor that
attaches the mount cover to the mount section and to
which the surgical instrument is to be mounted,
wherein
the mount cover includes a plurality of through holes and
is provided independently of the adaptor,
a protective film is attached to the second surface of the
mount cover so as to cover all of the plurality of
through holes, the protective film being configured to
be peelable from the mount cover, and
a length of the protective film is longer than a length of the
mount cover in the longitudinal direction.

16. The surgical robot according to claim 15, wherein
the pair of grip portions are arranged facing each other in
a direction sandwiching the mount cover along a direc-
tion orthogonal to the longitudinal direction of the
drape body.

17. The surgical robot according to claim 15, wherein
the drape body has a shape in which an end portion on the
other side of the drape body is linearly closed, wherein
a corner of the end portion on the other side of the drape
body is chamfered.

18. A sterile drape for covering a robot arm of a surgical
robot, comprising:
a bag-shaped drape body formed with an opening at an
end portion on one side of the drape body;
a pair of grip portions projecting outside from the end
portion on the one side of the drape body in a direction
parallel to a longitudinal direction of the drape body
and formed integrally with the drape body; and
a mount cover that is provided at the other side of the
drape body and is a flat resin plate including a first
surface and a second surface opposite to the first
surface, the first surface facing a mount section of the
robot arm and the second surface facing an adaptor that
attaches the mount cover to the mount section and to
which a surgical instrument is to be mounted, wherein
the mount cover includes a plurality of through holes,
a protective film is attached to the second surface of the
mount cover so as to cover all of the plurality of
through holes, and is configured to be peelable from the
mount cover,
the drape body and the mount cover are provided inde-
pendently of the adaptor, and
the protective film is peeled off after attaching the mount
cover to the mount section of the robot arm and
covering the robot arm with the drape body and before
attaching the adaptor to the mount section via the
plurality of through holes of the mount cover.

19. The sterile drape according to claim 18, wherein a
length of the protective film is longer than a length of the
mount cover in the longitudinal direction.

20. The sterile drape according to claim 18, wherein
the pair of grip portions are arranged facing each other in
a direction sandwiching the mount cover along a direc-
tion orthogonal to the longitudinal direction of the
drape body.

* * * * *